United States Patent [19]
Phelan

[11] Patent Number: 6,152,886
[45] Date of Patent: Nov. 28, 2000

[54] SUCTION DEVICE FOR USE DURING MEDICAL PROCEDURES AND THE LIKE

[76] Inventor: James C Phelan, 204 Shadow Lake Dr., Lilburn, Ga. 30047

[21] Appl. No.: 09/072,494

[22] Filed: May 5, 1998

[51] Int. Cl.[7] .................................................. A61B 10/00
[52] U.S. Cl. ............................ 600/571; 604/317; 433/91
[58] Field of Search .................................. 600/565, 578; 433/91; 604/317, 318, 319

[56] References Cited

U.S. PATENT DOCUMENTS

| | | | |
|---|---|---|---|
| 4,126,127 | 11/1978 | May | 600/187 |
| 5,151,094 | 9/1992 | Hanifl | 433/91 |

*Primary Examiner*—Gary O'Connor
*Assistant Examiner*—Pamela Wingood
*Attorney, Agent, or Firm*—Eric P. Schellin

[57] ABSTRACT

A suction device is disclosed comprising an elongated tubular metal handle portion having a predetermined uniform diameter suction bore therethrough and a spigot connection portion for connection to a hospital suction source. The device further comprises a selected metal probe having a predetermined uniform diameter suction passage therethrough and terminating in a suction tip. The inner diameter of the probe is less than the inner diameter of the handle portion. The proximal end of the probe has a non-metallic secured sleeve thereabout. The outer diameter of the sleeve is detailed to frictionally engage an inner wall end portion of the handle opposite to the spigot connection portion. The selected probe may be of varying diameters which is fitted with a selected diameter dimensioned sleeve whereby the probe fits within the selected and the probe carrying sleeve fits removably frictionally within the tubular metal handle. The handle has a controllable suction portion perpendicular to the handle whereby the suction at the tip of the probe can be controlled.

2 Claims, 2 Drawing Sheets

SUCTION DEVICE FOR USE DURING MEDICAL PROCEDURES AND THE LIKE

This invention relates to suction devices and in particular to such devices for medical, surgical or dental use.

BACKGROUND OF THE INVENTION

Suction devices are used for medical, surgical or dental use to remove foreign matter, fluid, blood, pus, mucous, polyps, bone particles, necrotic and cancerous matter and the like (all of which are hereinafter referred to as "waste matter"). Such suction devices are normally provided in two types via a suction nozzle comprising a rigid nozzle or a suction catheter comprising an elongated flexible catheter which can be inserted into a body cavity as desired. The nozzle or catheter is normally connected to a suction source via an intermediate member which is connected by connection means to a flexible tube that is connected to the suction source. The connection means being normally in the form of a hollow spigot portion. In the suction nozzle the intermediate member may comprise a handle which carries a probe.

In order that the degree of suction can be controlled, a suction port may be provided in the intermediate member leading to the suction passage therethrough and the medical personnel operating the suction device by obturating the suction port to a greater or lesser extent, can vary the suction at the tip of the probe.

BRIEF SUMMARY OF THE INVENTION

A controllable suction device of the invention includes an elongated metal conduit being a handle portion having a predetermined uniform internal diameter suction bore therethrough and a spigot connection portion connected to a hospital suction source. The device further comprises a selected metal tubular probe having a predetermined internally uniform diameter suction passageway therethrough and terminating in a suction tip. The inner diameter of the probe is less than the inner diameter of the handle portion. The proximal end of the probe has a non-metal friction fitted or adhesively secured sleeve mounted thereabout. The outer diameter of the sleeve is designed and dimensioned to frictionally engage an inner wall distal end portion of the handle opposite to the spigot end connection portion. The probe may be of a selected diameter which is fitted with a selected diameter dimensional sleeve whereby the probe fits frictionally or adhesively within the selected sleeve and the probe carrying sleeve fits removably frictionally within the distal portion of the tubular metal handle. The handle has a controllable suction port which is perpendicular to the handle whereby the suction at the tip of the probe can be hand controlled by placing a thumb over the port, for instance, when the handle is normally held.

The spigot end portion fits into an end portion of a flexible conduit, such as a rubber tube. The end portion of the said conduit is distended over the spigot. The flexible conduit has an internal diameter similar to the inner diameter of the handle. In this manner the passageway in the handle and the flexible conduit is uniformly the same and devoid of obstructions.

An object of the present invention is to provide an improved suction device.

It is a further object of this invention to provide a controllable suction assembly wherein the probe is made separate from the handle.

It is a further object of this invention to provide a suction device capable of being cleaned, processed and sterilized. Thereby eliminating any possibility of cross contamination not uncommon to surgical cannulated devices.

It is a further object of the invention to provide probes of various diameters that may be fitted as desired with sleeves of appropriate size to fit both the probes of choice and the internal diameter of the handle.

It is a further object of the invention to employ tubular metal probes which may be easily bent by the user to accommodate the situs of the area to the suction.

It is still a further object of the invention to provide a handle portion that may have a 30° bend and may be knurled externally or otherwise roughened for convenience of holding by the user.

It is yet a further object of the invention to provide a finger or thumb controllable suction port perpendicular to the handle. The port in one embodiment has a flat disc fitted about the port upon which the flat portion of the thumb of the user can be placed for valving as desired.

Other objects, advantages and features of the present invention will become apparent from the following specification when taken in conjunction with the accompanying drawings.

DESCRIPTION OF THE CURRENTLY PREFERRED EMBODIMENTS OF THE INVENTION

Figure 1:
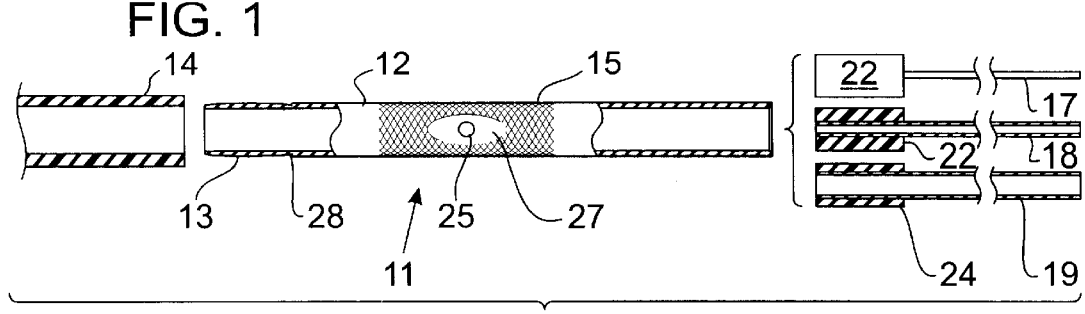
FIG. 1 is a fragmentary view, in partial cross section and exploded, of the suction device.

The suction device of the present invention is shown, generally, by reference numeral 11. It consists of an elongated metal tube 12 having a spigot proximal end 13 which is detailed to fit into a distendible flexible rubber tubing 14. The tubing 14 is shown only in a severely fragmentary condition in cross section. The other end, not shown, is secured to a conventional vacuum source found in all hospital locations. As a practical matter, tubing 14 may have interposed a sump by means of which waste matter being suctioned is diverted thereinto before the main suction is reached.

The metal tube 12 has a knurled section 15 positioned approximately midway the ends of tube 12. This knurled section is provided to provide a positive grip. The tube 12 constitutes a handle portion of the suction device.

As shown to the right of the said handle portion are three fragmentary probes 16 each of a different diameter with the smallest diameter probe 17 being at the top. The next probe 18, there below, and the largest diameter probe 19 being the lowest as depicted.

Each of the probes is affixed with a suitably dimensioned and diameter sleeve 21. The sleeve 22 depicts the sleeve in a side perspective. The sleeve 23, there below, is a cross-sectional view. Similarly, the sleeve 24 is also in cross-sectional view.

All three sleeves possess an outer diameter detailed to fit into the distal end of the handle tube 12 in a friction manner whereby the same handle may be employed for various probes as desired. It is relatively easy to change the probes 16. A salient feature of the present invention is to employ a single sized handle which can accommodate various probes of various longitudinal lengths and diameters.

It will be found desirable, due to the inexpensive nature of the probes, to dispose of the probes after they have been bent during use. The probes 17, 18 and 19 are constructed of aluminum. The sleeves 22, 23, 24 are constructed of a suitable polymeric material which can be either thermoplastic or thermosetting.

Figure 2:
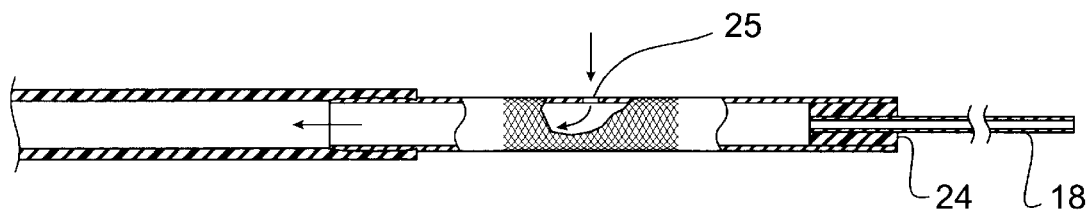
FIG. 2 is a fragmentary view, in partial cross section and fully assembled, of one embodiment of FIG. 1.

The handle 12 is constructed of 330 stainless steel. The handle is fitted with a hole 25 which is located in an area on the handle that is clear of the knurling 15. The hole 25 is where the valving occurs to control the suction. Note the arrows, from FIG. 2 showing flow of air through hole 25, as a result of the hook up of the handle 12 to flexible conduit 14 and fitment with probe 18 and its sleeve 23.

Figure 3:
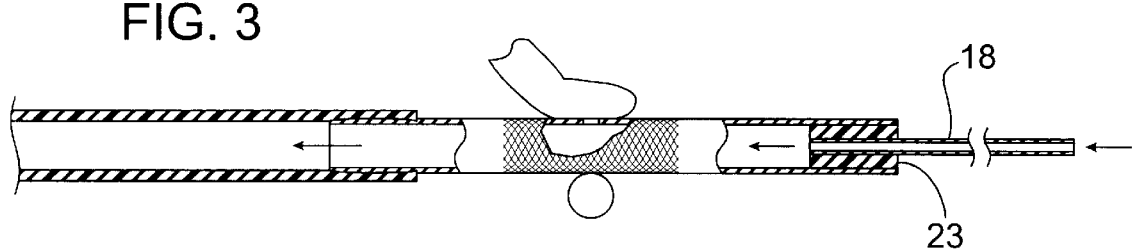
FIG. 3 is the same view as FIG. 2 wherein the suction port is in a finger controlled closed condition.

Then, in FIG. 3, one can see the use of a finger of a hand to obdurate the hole 25 so that further ingress of air occurs only through probe 18 and with the flow of air any debris that is picked up by the probe 18 as a consequence of the distal end of the probe 18 being positioned in a body cavity.

Figure 4:
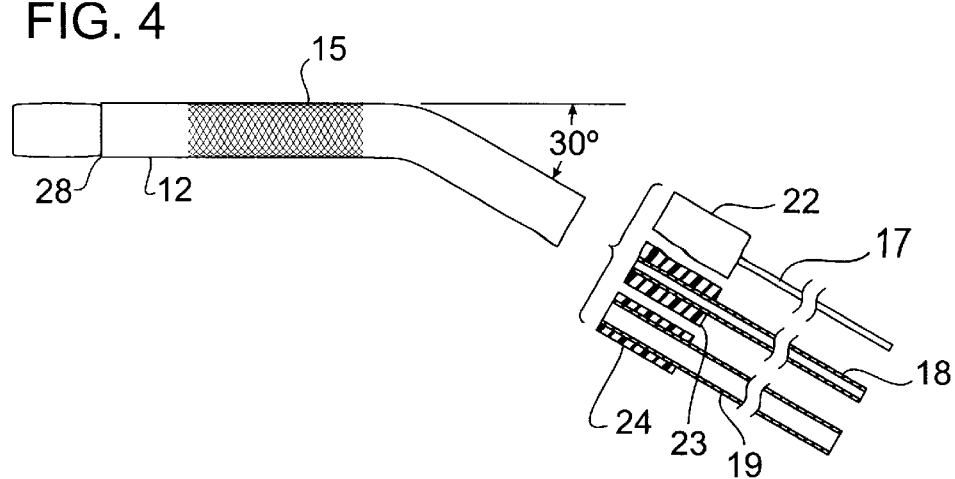
FIG. 4 is another embodiment, similar to FIG. 1, of the suction device in partial cross-suction.

Turning to FIG. 4, one can see another embodiment wherein the handle 12 is deflected at a 30° angle. It should be noted that probes 17, 18, 19 area identical to the probes 17, 18 and 19 of FIG. 1.

Figure 5:
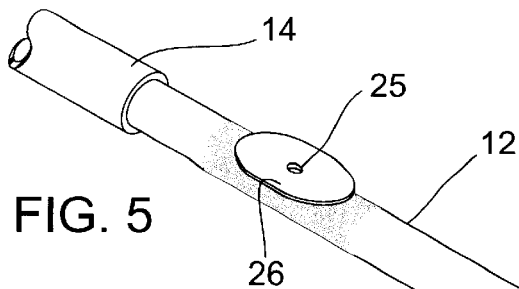
FIG. 5 is a perspective view of one embodiment of the present invention.
Figure 6:
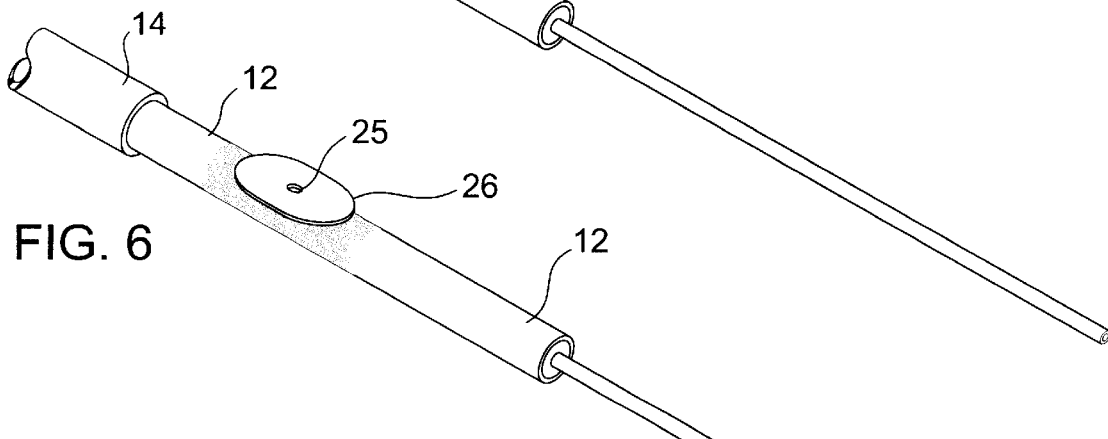
FIG. 6 is a perspective view of another embodiment with the probe in a bent condition.

FIGS. 5 and 6, show a suction device wherein the hole 25 is surrounded by a flat flange area 26 which is designed to accept the thumb of a user of the suction device of the present invention.

Then in FIG. 6, the probe 18 is bent to suit by the operator.

Figure 7:
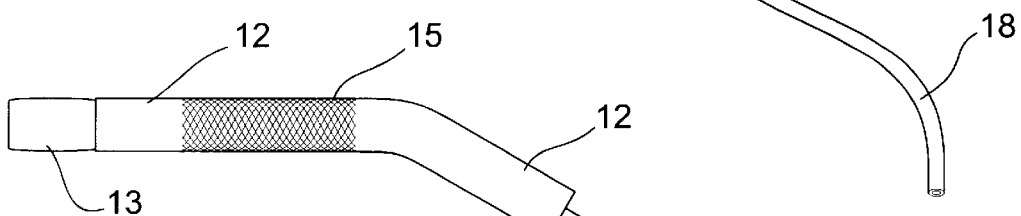
FIG. 7 is a perspective view with the tubular handle portion bent at an angle of 30°.

In FIG. 7 the handle 12 is seen to have 30° bend down stream after the hole 25, useful on some occasions to get the suction probe into a body cavity.

Figure 8:
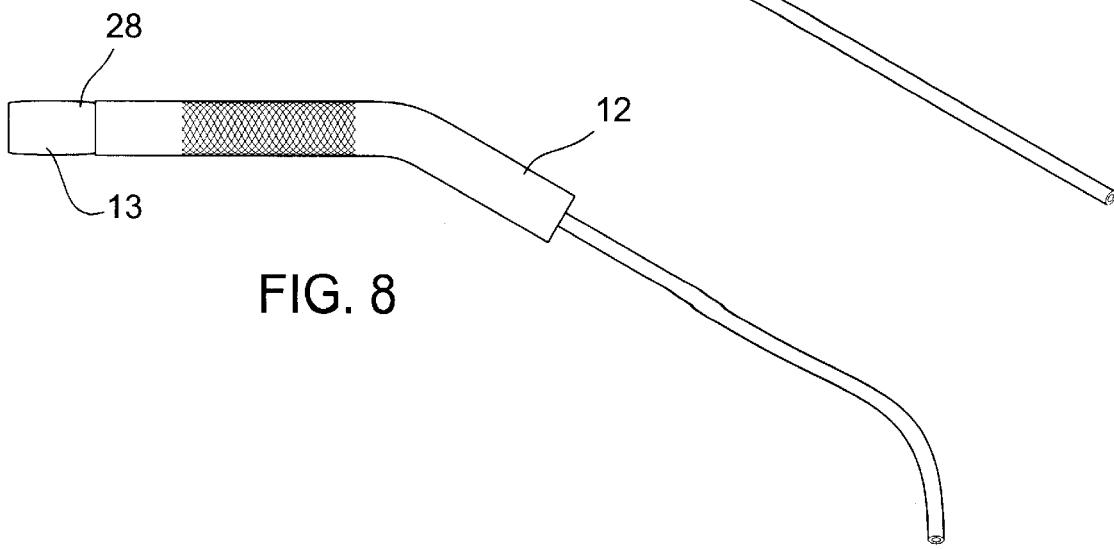
FIG. 8 is another perspective view showing the 30° bend in the tubular handle and showing a bend in the probe as well.

Finally, in FIG. 8 the bent handle is employed with a further bend in the probe 18.

It is contemplated that not only will the diameter of the probe be over a range but also the lengths of the probes will vary. For instance the length of the bore can be any selected but useful length. It has been found that the preferred range will be between 3 to 10 inches. The diameters of the bores will be from 3 to 12 French.

In the handle 12 the knurled area can be replaced with a sand blasted matte area.

It will be seen that the invention is to hand held suction devices with both straight and angled sections where the operator wishes intermittent or controlled suctioning. Furthermore, the device has been designed for broad based multi speciality applications.

The handle is manufactured of surgical grade stainless steel. The outer diameter of the handle is 5/16" (7.94 mm). The inner diameter of the handle is 1/4" (6.35 mm).

The inner diameter of the handle possesses no chamber, cavities or manufactured indentations throughout its length. The preferred length of the handle is about 3 1/4" (82.55 mm). Where angled the angulation imposed is about 30°. The place of angulation is about 1" from its distal end and its degree of angulation is about 30°. These parameters have been selected as least offending the integrity of the 1/4" (6.35 mm) inner lumen of the handle 12. The placed of angulation and the degree have been designed such to accept or accommodate all bristled 1/4" . (6.35 mm) brushes or ram rod cleaning devices.

Approximately 1 1/2 (38.1 mm) from the distal end of the control, the hole 25 approximately 0.09" (2.3 mm) is drilled into and through one wall of the handle 12. Where control is angled, the hole placement is on the top wall of the handle (away from the angle). The 25 hole possesses sufficient size for cleaning by brush, toothpick, etc.

The suction control surface may be of two or more types. In regard to FIGS. 5 and 6 an oval shaped plate 26 of highly polished surgical stainless steel with a hole of the same diameter as hole 25 is placed directly over it and close soldered to the handle. Glass beaded sand blasting is applied around the remaining unexposed circumference of the unit.

Dimensions: Distally (top) to Proximal (Bottom) 3/4" (19.1 mm)

(Across) 9/16" (14.3 mm)

(Thickness) 31/1000 (0.8 mm)

Attention is now directed to the embodiment in FIGS. 1 to 3 where only a direct hole 25 is provided. A dimple 27 is located approximately 1/3" (12.7 mm) proximately and distally from the activation hole 25.

The dimple is burnished into and around the hole 25.

The width: Approximately 3/16" (4.76 mm)

Burnished area" Oval shape

Burnished area with hole 25 is high polished finished.

Around much of the remaining circumference of the handle a mechanical knurling process is imposed on the handle.

Distance: Total 1 1/16" (26.9 mm) distal to proximately with hole 25 as center.

Both the dimple 27 imposed and the plate 26 affixed on the handle are highly finished. The remaining circumference has either sandblasting or knurling, effect is to provide a tactile identification of the hole 25.

The spigot 13 has from 1/2" (12.7 mm) from the proximal end a groove 28 etched into and around the circumference of the handle. About the groove 28 a high polish finish is applied. The said groove 28 provides easier acceptance and seating of the suction tubing 14 over the end of the handle 12 at the spigot portion 13.

The probes 17, 18 and 19 are constructed of malleable straight thin wall tubing. The larger bore of the handle is female in design. The probes are male in design.

The sleeves 22, 23 and 24 have a length of about 1/2" (12.7 mm) to 1 1/4" (31.75 mm), with a diameter of about 1/4" (6.35 mm).

The manufacture of the sleeve is accomplished by employing a DELRIN rod (an acetal thermoplastic resin) of about 1/4" (6.35 mm) diameter and a length, for example of 1/2" (12.7 mm).

A hole drilled through the center of the DELRIN rod, is slightly larger than the specific selected metal probe it is to accept. The metallic tube is placed and extends slightly beyond the distal end of the sleeve. The sleeves 22, 23 and 24 are glued in place to the end of the shaft of probe by suitable conventional adhesives.

The lesser hardness of the probe with its sleeve as compared to its female handle counterpart, i.e. steel, is a uniqueness of the present invention. For instance, the sleeve being a polymer constitutes a good electrical insulator to protect the user. This, thereby, expands the devices' versatility into the realm of electrosurgical suctioning applications.

When the probe is joined through its respective sleeve (whether straight or angled handle) if its angle or direction is acceptable as it is to the user, the probe need not be bent.

Of course, a straight tube is far easier to clean, flush, scrub and sterilize, than a bent one. Therefore a used unbent tube can easily and competently be reprocessed for reuse. Diameter enters this discussion process, i.e., 3FR, 5FR may automatically be discarded. These sizes are so small in diameter that effective cleaning is problematical.

It is pointed out that in hospital/clinic/office settings several different size suction probes are often utilized in the same procedure on the same patient. In those instances, the universality of the handle becomes all the more apparent.

Malleabillity of the probe gives the clinician several distinct advantages. (1) It allows the clinician to customize the suction to best anatomical advantage. (2) It save the time of mid-procedure suction changes where angle and not diameter is the issue.

The suction devices can be put to other uses with or without modification for such purposes. Thus they may be used for sucking, removing or transferring matter in a controlled manner in industrial or laboratory conditions without the operator having his/her finger contaminated thereby.

The invention now being fully described, it will be apparent to one of ordinary skill in the art that many changes and modifications can be made thereto without departing from the spirit or scope of the invention as set further in the following claims.

What is claimed is:

1. A suction device comprising:
    a) a suction tubular probe having distal and proximal ends, an internal uniform diameter bore terminating at a suction tip at the distal end thereof;
    b) a tubular handle having distal and proximal ends and an internal uniform diameter bore;
    c) said tubular handle having a controllable suction port;
    d) the said external diameter of said tubular probe being less than the internal diameter of the tubular handle;
    e) a sleeve having a proximal end and a distal end;
    f) said sleeve having an outer diameter substantially the same as the inner diameter of the bore of said tubular handle;
    g) said sleeve having an internal diameter adapted and constructed whereby the proximal end of said probe fits internally of said sleeve;
    h) said probe at said proximal end terminates contiguous with said proximal end of said sleeve;
    i) said sleeve being adhesively secured to said proximal ends of said probe;
    j) said proximal end of said probe mounted with said sleeve being frictionally engaged within the bore of the distal end of said handle;
    k) the tubular handle has an approximately 30 degree angularity whereby the tubular handle is divided into a major portion and a minor portion, the major portion terminating in the proximal end and the minor portion terminating in the distal end;
    l) said controllable suction port being located in said major portion of said tubular handle;
    m) said controllable suction port being surrounded by an affixed stainless disc adapted and constructed to accept the surface of the thumb of a user and being integrally tangentially with respect to said tubular handle.

2. A suction device comprising:
    a) a suction tubular probe having distal and proximal ends, an internal uniform diameter bore terminating at a suction tip at the distal end thereof;
    b) a tubular handle having distal and proximal ends and an internal uniform diameter bore;
    c) said tubular handle having a controllable suction port;
    d) the said external diameter of said tubular probe being less than the internal diameter of the tubular handle;
    e) an acetal resin sleeve having a proximal end and a distal end;
    f) said sleeve having an outer diameter substantially the same as the inner diameter of the bore of said tubular handle;
    g) said sleeve having an internal diameter adapted and constructed whereby the proximal end of said probe fits internally of said sleeve;
    h) said probe at said proximal end terminates contiguous with said proximal end of said sleeve;
    i) said sleeve being adhesively secured to said proximal ends of said probe;
    j) said proximal end of said probe mounted with said sleeve being frictionally engaged within the bore of the distal end of said handle;
    k) the tubular handle has an approximately 30 degree angularity whereby the tubular handle is divided into a major portion and a minor portion, the major portion terminating in the proximal end and the minor portion terminating in the distal end;
    l) said controllable suction port being located in said major portion of said tubular handle;
    m) said controllable suction port being surrounded by an affixed stainless disc adapted and constructed to accept the surface of the thumb of a user and being integrally tangential with respect to said tubular handle.

* * * * *